United States Patent
Lin et al.

(10) Patent No.: US 10,376,461 B2
(45) Date of Patent: Aug. 13, 2019

(54) BRANCHED POLYETHER-POLYAMIDE BLOCK COPOLYMERS AND METHODS OF MAKING AND USING THE SAME

(75) Inventors: Geng Lin, Rochester Hills, MI (US); Nancy W. Harman, Savannah, GA (US)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/233,232

(22) PCT Filed: May 18, 2012

(86) PCT No.: PCT/US2012/038606
§ 371 (c)(1),
(2), (4) Date: Jan. 16, 2014

(87) PCT Pub. No.: WO2013/012476
PCT Pub. Date: Jan. 24, 2013

(65) Prior Publication Data
US 2014/0140939 A1 May 22, 2014
US 2015/0098912 A9 Apr. 9, 2015

Related U.S. Application Data

(60) Provisional application No. 61/510,223, filed on Jul. 21, 2011.

(51) Int. Cl.
| | | |
|---|---|---|
| C08L 77/00 | (2006.01) | |
| A61K 8/90 | (2006.01) | |
| C08G 65/333 | (2006.01) | |
| C08G 69/40 | (2006.01) | |
| C08L 63/00 | (2006.01) | |
| A61Q 17/04 | (2006.01) | |
| A61Q 19/00 | (2006.01) | |
| A61K 8/88 | (2006.01) | |
| C08G 69/48 | (2006.01) | |
| A61Q 1/02 | (2006.01) | |
| A61Q 5/00 | (2006.01) | |
| A61Q 11/00 | (2006.01) | |
| A61Q 15/00 | (2006.01) | |

(52) U.S. Cl.
CPC .................. *A61K 8/90* (2013.01); *A61K 8/88* (2013.01); *A61Q 17/04* (2013.01); *A61Q 19/00* (2013.01); *C08G 65/33303* (2013.01); *C08G 69/40* (2013.01); *C08G 69/48* (2013.01); *C08L 63/00* (2013.01); *A61Q 1/02* (2013.01); *A61Q 5/00* (2013.01); *A61Q 11/00* (2013.01); *A61Q 15/00* (2013.01); *C08G 2650/50* (2013.01)

(58) Field of Classification Search
CPC ............ C08L 77/06; C08L 77/12; A61K 8/90
See application file for complete search history.

(56) References Cited

U.S. PATENT DOCUMENTS

| | | | |
|---|---|---|---|
| 4,717,763 A * | 1/1988 | Coquard et al. ............... 528/324 | |
| 5,254,668 A | 10/1993 | Dominguez et al. | |
| 5,342,918 A | 8/1994 | Howelton et al. | |
| 5,349,011 A | 9/1994 | Reichert | |
| 5,399,663 A | 3/1995 | Clark, II | |
| 6,111,055 A | 8/2000 | Berger | |
| 6,169,160 B1 | 1/2001 | MacQueen | |
| 6,399,713 B1 | 6/2002 | MacQueen | |
| 6,906,165 B2 | 6/2005 | DiSilvestro | |
| 7,445,770 B2 | 11/2008 | Berezkin | |
| 8,058,386 B2 | 11/2011 | Pavlin | |
| 9,074,685 B2 | 7/2015 | Strack | |
| 2002/0028857 A1 | 3/2002 | Holy | |
| 2003/0065084 A1 | 4/2003 | MacQueen et al. | |
| 2004/0204520 A1 | 10/2004 | Bell | |
| 2005/0267231 A1 | 12/2005 | Pavlin | |
| 2008/0070025 A1* | 3/2008 | Pavlin .................... A61L 9/012 428/304.4 |
| 2009/0074685 A1 | 3/2009 | Lai | |
| 2010/0069286 A1* | 3/2010 | Pavlin .............................. 512/4 | |
| 2011/0117156 A1* | 5/2011 | Lin ........................... A61L 9/01 424/409 |
| 2011/0318479 A1 | 12/2011 | Reddington | |
| 2012/0029559 A1 | 2/2012 | Lee | |

FOREIGN PATENT DOCUMENTS

| | | |
|---|---|---|
| EP | 1616896 | 1/2006 |
| JP | 47034592 | 11/1972 |
| JP | 61138628 | 6/1986 |
| JP | S61-138628 | 6/1986 |
| JP | 06065369 | 3/1994 |
| JP | H06-065369 | 3/1994 |
| JP | 08020764 | 1/1996 |
| JP | H08-020764 | 1/1996 |
| JP | 2001502742 | 2/2001 |
| JP | 2004506080 | 2/2004 |

(Continued)

OTHER PUBLICATIONS

International Search Report for PCT.US2012/038606, European Patent Office (EPO), dated Mar. 13, 2013.

(Continued)

*Primary Examiner* — Gregory Listvoyb
(74) *Attorney, Agent, or Firm* — RatnerPrestia

(57) ABSTRACT

Described herein is a polyether polyamide block copolymer as well compositions and products containing the polyether polyamide block copolymer. Methods of making and using the copolymer, the compositions, and products are also described herein.

15 Claims, No Drawings

(56) References Cited

FOREIGN PATENT DOCUMENTS

| | | |
|---|---|---|
| JP | 2004518006 | 6/2004 |
| JP | 2004295120 | 10/2004 |
| JP | 2005112790 | 4/2005 |
| JP | 2007186590 | 7/2007 |
| JP | 2008500432 | 1/2008 |
| JP | 2008231424 | 10/2008 |
| JP | 2010196041 | 9/2010 |
| JP | 2010539189 | 12/2010 |
| JP | 2011084737 | 4/2011 |
| JP | 2012503044 | 2/2012 |
| WO | WO 1998/17243 | 4/1998 |
| WO | 00041188 | 7/2000 |
| WO | 2005118008 | 12/2005 |

OTHER PUBLICATIONS

Japanese Office Action dated Jan. 5, 2016 for Japanese Application No. 2014-521621.
Japanese Office Action dated Apr. 26, 2016 for Application No. 2014-521621, 3 pages.

* cited by examiner

BRANCHED POLYETHER-POLYAMIDE BLOCK COPOLYMERS AND METHODS OF MAKING AND USING THE SAME

BACKGROUND

Personal care products can include one or more active ingredients in a liquid base or carrier. The rheology and structure of the base impacts the form, flow, and spreading capability of the product. Thus, the base largely determines the manner in which the consumer can use the product. For some consumer uses, products are desired that maintain their shape when undisturbed but flow when agitated. As such, gelling components are needed to include in these personal care products without counteracting the active ingredients.

SUMMARY

Described herein are compositions and products containing a polyether polyamide block copolymer and methods of making and using the same. The polyether polyamide block copolymer has the following formula:

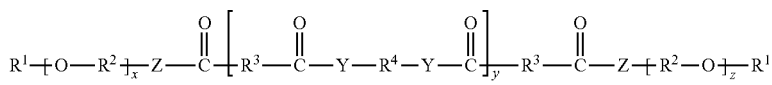

wherein $R^1$ is a $C_1$-$C_8$ hydrocarbon radical, $R^2$ is a $C_2$-$C_4$ hydrocarbon diradical, $R^3$ is a $C_2$-$C_{52}$ hydrocarbon diradical, $R^4$ is selected from $C_2$-$C_{12}$ hydrocarbon diradicals optionally substituted with alkylene oxide groups, wherein at least a portion of the $R^4$ groups is substituted with Y—C(=O)—$R^3$—C(=O)—Z—($R^2$—O)$_w$—$R^1$, wherein Y is O or NH, Z is O or NH, w is an integer from 2 to 100; x is an integer from 2 to 100; y is an integer from 1 to 10, and z is an integer from 2 to 100, and wherein at least a portion of the Y groups is NH. In some embodiments, in at least a portion of the $R^4$ groups substituted with Y—C(=O)—$R^3$—C(=O)—Z—($R^2$—O)$_w$—$R^1$, Y is O. For example, at least a portion of the $R^4$ groups can be a $C_3$ diradical substituted with O—C(=O)—$R^3$—C(=O)—Z—($R^2$—O)$_w$—$R^1$. In other embodiments, in at least a portion of the $R^4$ groups substituted with Y—C(=O)—$R^3$—C(=O)—Z—($R^2$—O)$_w$—$R^1$, Y is NH. For example, at least a portion of the $R^4$ groups can be a $C_6$ diradical substituted with alkylene oxide groups and NH—C(=O)—$R^3$—C(=O)—Z—($R^2$—O)$_w$—$R^1$. In some examples, the weight average molecular weight is from 5000 to 30,000. Further, in some examples, the softening point is from 60° C. to 140° C.

Also described herein are polyether polyamide block copolymers according to the formula shown above produced by reacting a dibasic acid; a $C_2$-$C_2$ aliphatic diamine; a tri-functional component selected from the group consisting of triols, triamines, and mixtures thereof; and a monofunctional poly(alkyleneoxy)monoamine. In some embodiments, the trifunctional component includes glycerin. In some embodiments, the trifunctional component includes a poly(alkyleneoxy)triamine. Optionally, the trifunctional component is a $C_6$ triamine substituted with oxypropylene groups. In some examples, the weight average molecular weight is from 5000 to 30,000.

Further described herein is a method of preparing a polyether polyamide block copolymer. The methods include reacting a dibasic acid, a $C_2$-$C_{12}$ aliphatic diamine, a tri-functional component, and a monofunctional poly(alkyleneoxy)monoamine. The tri-functional component can be selected from the group consisting of triols, triamines, and is mixtures thereof. In some embodiments, the trifunctional component includes glycerin. In some embodiments, the trifunctional component includes a poly(alkyleneoxy)triamine. In some embodiments, the reacting step is conducted at a temperature of from 200° C. to 250° C. for from 2-8 hours. The amount of dibasic acid in said reacting step can be, for example, from 40-50% by weight of the reactants.

A composition formed by mixing a polar liquid and a polyether polyamide block copolymer as described herein is also provided herein. In some examples, the composition is a gel at 25° C. The composition can further include a fragrance oil.

Further provided are controlled release products including the composition. The controlled release product can further include a bio-active solid or liquid component dissolved in the polar liquid. Personal care products including the composition are also provided. The personal care products can optionally include a UV filter.

Methods of making a gel composition are also provided herein. The methods include mixing a polar liquid and a polyether polyamide block copolymer described herein at a temperature of from 80° C. to 140° C. until the copolymer is substantially dissolved in the liquid medium; and allowing the mixture to cool to ambient temperature to produce a gel.

The details of one or more embodiments are set forth in the description below. Other features, objects, and advantages will be apparent from the description and from the claims.

DETAILED DESCRIPTION

Polyether polyamide block copolymers and methods for their preparation and use are described herein. The polyether polyamide block copolymers can have a structure represented by Formula I:

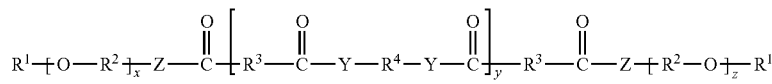

(Formula I)

In Formula I, $R^1$ is a $C_1$-$C_8$ hydrocarbon radical. As used herein, a hydrocarbon group contains carbon and hydrogen atoms. Hydrocarbon groups can be formed from one or more of aliphatic and aromatic moieties. Suitable aliphatic moieties for use in the copolymers described herein include alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. Aromatic moieties are also referred to herein as aryl groups.

As used herein, alkyl, alkenyl, alkynyl, cycloalkyl, cycloalkenyl, and cycloalkynyl are monovalent radicals, while alkylene, alkenylene, alkynylene, cycloalkylene, cycloalkenylene, and cycloalkynylene are polyvalent radicals. As used herein alkyl, alkylene, cycloalkyl, and cycloalkylene are saturated radicals, while alkenyl, alkenylene, alkynyl, alkynylene, cycloalkenyl, cycloalkenylene, cycloalkynyl, and cycloalkynylene are unsaturated radicals. The alkyl, alkylene, alkenyl, alkenylene, alkynyl, and alkynylene moieties can be straight chain or branched. The cycloalkyl, cycloalkenyl, cycloalkynyl, cycloalkylene, cycloalkenylene and cycloalkynylene moieties can be monocyclic or polycyclic, where a polycyclic moiety can be, for example, bicyclic or tricyclic.

Exemplary alkyl moieties include methyl, ethyl, propyl, hexyl, and 2-ethylhexyl. Exemplary alkylene moieties include, for example, methylene, methylidene, and ethylene. Examples of suitable cycloalkyl groups include cyclohexyl and norbornyl. Aromatic moieties suitable for the copolymers described herein can be monocyclic or polycyclic. An exemplary monocyclic aryl group is phenyl, while exemplary polycyclic aryl groups include naphthyl. The aromatic moiety can be monovalent, e.g., phenyl, or polyvalent, e.g., phenylene.

Optionally, the hydrocarbon group can be a combination of aromatic and aliphatic groups, such as, for example, benzyl (phenyl-$CH_2$—, an arylalkylene group), tolyl ($CH_3$-phenylene-, an alkylarylene group), and xylyl (($CH_3$)$_2$-phenylene-, a dialkylarylene group). In some examples, the hydrocarbon group can be a combination of two or more aromatic groups, e.g., biphenyl (phenyl-phenylene-, an arylarylene group).

In Formula I, $R^2$ is a $C_2$-$C_4$ hydrocarbon diradical as discussed in more detail herein.

In Formula I, $R^3$ is a $C_2$-$C_{52}$ hydrocarbon diradical as discussed in more detail herein.

Further, in Formula I, $R^4$ is selected from $C_2$-$C_{12}$ hydrocarbon diradicals. In some embodiments, the diradicals can optionally be substituted with alkylene oxide groups, e.g., $R^4$ can be a $C_6$ diradical substituted with ethylene oxide groups. In some embodiments, at least a portion of the $R^4$ groups is substituted with the following structure represented by Structure A:

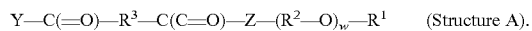

Y—C(=O)—$R^3$—C(C=O)—Z—($R^2$—O)$_w$—$R^1$ (Structure A).

In Structure A, Y is O or NH and Z is O or NH.
Also in Structure A, w is an integer from 2 to 100.
In some examples of Formula I, at least a portion of the Y groups is O. In these examples, at least a portion of the $R^4$ groups can be substituted with the following structure represented by Structure B:

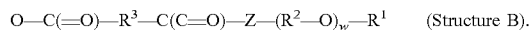

O—C(=O)—$R^3$—C(C=O)—Z—($R^2$—O)$_w$—$R^1$ (Structure B).

In some embodiments, $R^3$ can be a $C_3$ diradical.

In other examples of Formula I, at least a portion of the Y groups is NH. In these examples, at least a portion of the $R^4$ groups can be substituted with the following structure represented by Structure C:

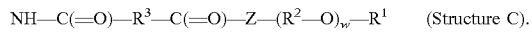

NH—C(=O)—$R^3$—C(=O)—Z—($R^2$—O)$_w$—$R^1$ (Structure C).

In some embodiments, $R^3$ can be a $C_6$ diradical optionally substituted with alkylene oxide groups.

Further, in Formula I, x is an integer from 2 to 100, y is an integer from 1 to 10, and z is an integer from 2 to 100.

The block copolymer of Formula I includes two terminal hydrocarbon groups, two polyether blocks, and one branched block. The branched block is provided by introducing a tri-functional group into the block copolymer as described herein. Thus, the block copolymers according to Formula I are not linear copolymers. The branched block can either be a branched polyamide block or a branched poly(ester-amide) block. The components of the copolymers can be incorporated into the copolymers by reacting together a monofunctional poly(alkyleneoxy)monoamine, a dibasic acid, an aliphatic diamine, and a tri-functional component including three groups selected from the group consisting of hydroxyl groups, amine groups and mixtures of these (e.g., a triol, a triamine, or a mixture of these).

As noted above. $R^1$ is a $C_1$-$C_8$ hydrocarbon radical. As such, the polyether polyamide block copolymers are terminated by hydrocarbon groups on each end of the copolymers. In some examples, $R^1$ is a $C_2$-$C_7$ hydrocarbon radical. In some examples, $R^1$ is a $C_3$ to $C_6$ hydrocarbon radical. In other examples, $R^1$ is a $C_4$ to $C_5$ hydrocarbon radical. $R^1$ can be, for example, a branched or straight-chained alkyl group. As such, the $R^1$ group contains at least one carbon. In some examples, $R^1$ is methyl.

The polyether polyamide block copolymer described herein also contain at least two polyether blocks connected to each terminal hydrocarbon group. As its name implies, a polyether block contains two or more ether groups. In other words, a polyether block contains the repeating formula [—O—$R_2$-]$_x$ where $R^2$ is a $C_2$-$C_4$ hydrocarbon diradical and x is an integer from 2 to 100. In some examples, $R^2$ is an alkylene group and can be propylene, ethylene, butylene, or a combination thereof to form propylene oxide, ethylene oxide, or butylene oxide groups in the polyether polyamide block copolymer.

Each polyether component of the block copolymer repeats from 2 to 100 times. For example, the polyether component can repeat from 5 to 90 times, from 10 to 80 times, from 20 to 70 times, from 30 to 60 times, or from 40 to 50 times. In some examples, the polyether component of the block copolymer can repeat 5 or more times, 10 or more times, 20 or more times, 30 or more times, 40 or more times, or 50 or more times. In other examples, the polyether component of the block copolymer can repeat less than 100 times, less than 90 times, less than 80 times, less than 70 times, less than 60 times, less than 50 times, less than 40 times, less than 30 times, less than 20 times, or less than 10 times. Optionally, the number of repeating polyether components can be determined upon the desired molecular weight of the component. In some examples, the polyether component of the block copolymer has a molecular weight (measured as either number or weight average) of less than 10,000. In another aspect, the molecular weight is between 100 and 4,000.

The $R^1$ and $R^2$ groups of the polyether polyamide block copolymers can be incorporated into the copolymers through a monofunctional poly(alkyleneoxy)monoamine. The monofunctional poly(alkyleneoxy)monoamine, also known as a polyoxyalkyleneamine, can contain one primary amine group and can be represented by the formula $R^1$—(O—$R^2$)$_x$—W wherein W is an amine and $R^2$ is one or more of ethylene, propylene, and n-butylene, each independently selected at each occurrence. These compounds are generally well-known to one of ordinary skill in the art and can be readily prepared by methodology described in the scientific and patent literature. For example, a monohydric initiator, i.e., a compound of the formula $R^1$—OH, can be reacted with an alkylene oxide (an $R^2$ group is derived from an epoxide-containing group), e.g., ethylene oxide, propylene oxide, etc., to provide a compound of the formula $R^1$—(O—$R^2$)$_x$—OH. This $R^1$-terminated polyalkylene glycol can then be subjected to reaction conditions to convert the terminal hydroxyl group to a terminal amino group, e.g., ammonia and hydrogen.

Commercially-available polyoxyalkyleneamines are typically prepared from ethylene oxide and/or propylene oxide and are available in varying ratios of propylene oxide-to ethylene oxide-based residues. Polyoxyalkyleneamines may be obtained from, e.g., BASF Corp. (Florham Park, N.J.) and Huntsman Chemical (Salt Lake City, Utah). Commercially available polyoxyalkyleneamines and selected properties are provided in Table A. In Table A, both XTJ and JEFFAMINE are product identifiers used by Huntsman Chemical. In Table A, $R^1$ is H (when ethylene oxide (EO) is the reactant) or —$CH_3$ (when propylene oxide (PO) is the reactant). Table A also provides the PO/EO ratio in the designated polyoxyalkyleneamine. In some examples, the monofunctional poly(alkyleneoxy)monoamine is JEFFAMINE M-2070, commercially available from Huntsman Chemical.

TABLE A

Typical Polyoxyalkyleneamines and Their Properties

| amine | $R^1$ | $R''$ | PO/EO (mole ratio) | MW | $T_m$ (° C.) |
|---|---|---|---|---|---|
| XTJ-505 | $CH_3$ | $CH_3$ | 9/1 | 600 | −40 |
| XTJ-506 | $CH_3$ | $CH_3$ | 3/19 | 1,000 | 29 |
| XTJ-507 | $CH_3$ | $CH_3$ | 39/6 | 2,000 | −36 |
| XTJ-508 (formerly JEFFAMINE ® M-2070 | $CH_3$ | $CH_3$ | 10/32 | 2,000 | 17 |
| XTJ 234 | $CH_3$ | $CH_3$ | 8/49 | 3000 | 36 |
| Diglycol amine | H | H | 0/2 | 105 (m = 0) | |

The polyether components of the polyamide block copolymer according to Formula I are connected to carbonyl groups. These carbonyl groups are linked to the $R^3$ groups. As noted above, the $R^3$ groups are $C_2$-$C_{52}$ dihydrocarbon radicals. One of the $R^3$ groups is included in the branched block of the copolymer according to Formula I. In some examples, the branched block is a branched polyamide block. In other examples, the branched block is a branched poly(ester-amide) block.

As its name implies, the branched polyamide block contains a plurality of amide groups. In the polyamide block, two or more amide groups are separated by hydrocarbon groups. In other words, a polyamide block contains the repeating formula [—$R^3$—(C=O)—Y—$R^4$—Y—(C=O)—]$_y$, where Y is NH and y is an integer from 2 to 100. As described above, $R^3$ is a $C_2$-$C_{52}$ hydrocarbon radical and $R^4$ is a $C_2$-$C_{12}$ hydrocarbon diradical. Some of the hydrocarbon groups of $R^4$ are optionally substituted, i.e., branched, with groups according to Structure C shown above. Copolymers containing the branched polyamide block can be referred to as polyalkyleneoxy polyamide (PAOPA) block copolymers.

Alternatively, the branched block of the copolymer can be a branched poly(ester-amide) block. In the poly(ester-amide) block, a combination of ester groups and amide groups are present and are separated by hydrocarbon groups. A poly(ester-amide) block contains the repeating formula [—$R^3$—(C=O)—Y—$R^4$—Y—(C=O)—]$_y$, where Y can be NH or O and y is an integer from 2 to 100. In these examples, the hydrocarbon groups of $R^4$ are branched with a combination of branching groups. Branching groups include, for example, groups according to Structure B or Structure C shown above. Copolymers containing the branched poly(ester-amide) block can be referred to as polyether poly(ester-amide) (PAOPEA) block copolymers.

In some examples, $R^3$ of the branched polyamide block or branched poly(ester-amide) block includes $R^3$ groups having at least 30 carbons. For example, $R^3$ can have at least 32 carbons, at least 34 carbons, at least 36 carbons, at least 38 carbons, at least 40 carbons, at least 42 carbons, at least 44 carbons, at least 46 carbons, at least 48 carbons, or at least 50 carbons. In some examples, the polyamide block includes $R^3$ groups having 30-42 carbons.

Optionally, the branched block includes $R^3$ groups formed from fatty acid polymerization. Fatty acids derived from vegetable oils, tallow, and tall oil (the latter are known as tall oil fatty acids, or TOFA) are commonly subjected to thermal polymerization, typically in the presence of a clay catalyst, to provide a commercially-available product known as dimer acid. These fatty acids contain 18 carbons, so that the corresponding dimer acid consists mainly of $C_{36}$ dicarboxylic acids. This dimer acid can be denoted by the structure HOOC—$C_{34}$—COOH, where the $C_{34}$ group is an exemplary $R^3$ group. $C_{34}$ is a mixture of isomeric structures, as more fully described in detailed descriptions of dimer acid, as found in, for example, Naval Stores—Production, Chemistry and Utilization, D. F. Zinkel and J. Russel (eds.), Pulp. Chem. Assoc. Inc., 1989, Chapter 23.

Suitable polymerized fatty acids are available commercially as, for example, UNIDYME dimer acid, from Arizona Chemical (Jacksonville, Fla.); EMPOL dimer acid from Henkel Corporation (now Cognis, Cincinnati, Ohio); and PRIPOL dimer acid from Unichema North America (Chicago, Ill.).

Commercially available dimer acid typically contains by-products of the fatty acid polymerization process. One common byproduct is the so-called trimer acid, which results when three fatty acid molecules react together to form a $C_{64}$ tricarboxylic acid. It is possible, in the preparation of a block copolymer as described herein, that two of the carboxylic acid groups of trimer acid will react with, e.g., a diamine, leaving one carboxylic acid group unreacted. When this occurs, the block copolymer will contain a carboxylic acid-substituted $R^3$ group. Accordingly, the block copolymers described herein can contain carboxylic acid-substituted hydrocarbon groups. For convenience, as used herein, $C_{34}$ refers to the incorporation of dimer acid into a polyamide block and further includes the reaction product of some trimer acid that may be a by-product in the commercial dimer acid.

Optionally, $R^3$ of the branched block can be formed from a combination of dimer acid and a co-diacid. As used herein, a co-diacid is a compound of formula HOOC—$R^3$—COOH where $R^3$ is not $C_{34}$ as defined above. In one aspect, the branched block in the copolymers of Formula I includes $R^3$ groups having 2-32 carbons, which are referred to herein a co-diacid $R^3$ groups. Suitable co-diacids have a linear $C_{4-12}$ hydrocarbon group between the two carboxylic acid groups, and more preferably have a linear $C_{6-8}$ hydrocarbon group. Linear diacids suitable for use as co-diacids include 1,6-hexanedioic acid (adipic acid); 1,7-heptanedioic acid (pimelic acid); 1,8-octanedioic acid (suberic acid); 1,9-nonanedioic acid (azelaic acid); 1,10-decanedioic acid (sebacic acid); 1,11-undecanedoic acid; 1,12-dodecanedioic acid (1,10-decanedicarboxylic acid); 1,13-tridecanedioic acid (brassylic acid); and 1,14-tetradecanedioic acid (1,12-dodecanedicarboxylic acid).

Another exemplary co-diacid suitable for use as described herein includes the reaction product of acrylic or methacrylic acid (or the ester thereof, with a subsequent hydrolysis step to form an acid) and an unsaturated fatty acid. For example, a $C_{21}$ diacid of this type can be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids can also be used as the co-diacid. An "aromatic diacid" as used herein refers to a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid can contain aliphatic carbons bonded to the aromatic ring(s), as in HOOC—$CH_2$—Ar—$CH_2$—COOH and the like. The aromatic diacid can contain two aromatic rings. In some examples, the two aromatic rings are joined together through one or more carbon bonds, (e.g., biphenyl with carboxylic acid substitution). In some examples, the two aromatic rings can be fused (e.g., naphthalene with carboxylic acid substitution).

In some examples, the $C_{34}R^3$ groups constitute at least 50 mol % of the total of the $R^3$ groups. For example, the $C_{34}R^3$ groups can constitute at least 60 mol %, at least 70 mol %, at least 80 mol %, at least 90 mol %, or at least 95 mol % of the $R^3$ groups. Accordingly, dimer acid can contribute at least 50% of the diacid equivalents, at least 60%, at least 70%, at least 80%, at least 90%, or at least 95% of the diacid equivalents in the branched block of the copolymer of Formula 1. In some examples, only dimer acid is used to form the branched block of the copolymer, i.e., no co-diacid is among the reactants. In some examples, the branched block is prepared with only co-acid and no dimer acid.

In some examples, $R^3$ can be a cyclohexane group. Accordingly, the branched block can contain a cyclohexane diradical between at least two carbonyl groups. The carbonyl groups can be located at opposite carbons of the cyclohexane group, e.g., carbons 1 and 4 of the cyclohexane group. In some examples, all of the $R^3$ groups in the block copolymer contain the cyclohexyl group. In other examples, at least 50% or at least 25% of the $R^3$ groups in the block copolymer contain the cyclohexyl group. The cyclohexyl $R^3$ group can be introduced into the copolymer as described herein by including cyclohexanedicarboxylic acid (CHDA) among the copolymer-forming reactants. CHDA, including 1,4-CHDA, is commercially available from many sources, e.g., Aldrich (Milwaukee, Wis.).

At least a portion of the branched block of the copolymer contains —NH—$R^4$—NH-moieties. As described above, $R^4$ is a hydrocarbon group. In some examples, the $R^4$ hydrocarbon group has between 2 and 12 carbons. $R^4$ can be, for example, an alkylene group such as a straight-chained alkylene group. In one aspect, the branched block includes $R^4$ groups having 2 to 6 carbons. In another aspect, at least 50% of the $R^4$ groups have 2 to 6 carbons. In a further aspect, all of the $R^4$ groups have 2 to 6 carbons.

In examples where at least 50% of the $R^3$ groups are cyclohexane diradicals, then the $R^4$ group can have at least 6 carbons. Not to be bound by theory, this is because when $R^4$ has only 2-4 carbons, the melting point of the resin tends to increase. Likewise, as more of the $R^3$ groups are cyclohexane diradical, the melting point of the resin tends to increase. Accordingly, when at least about 50% of the $R^3$ groups are cyclohexane diradical, then most if not all of the $R^4$ groups should have at least 6 carbons in order to counteract the melting point-increasing effect of the cyclohexane diradical.

In some examples, $R^4$ is optionally substituted with alkylene oxide groups (i.e., polyether groups) in addition to the substitution that occurs in the branched groups (i.e., the $R^4$ groups substituted with $(R^2—O)_w$). The polyether component of the $R^4$ portion of the block copolymer can have a molecular weight (number or weight average) of less than 10,000. For example, the molecular weight of the $R^4$ polyether component can be between 100 and 4,000.

At least a portion of the $R^4$ groups can be further substituted with a branching unit of the Structure A. In some examples, the branching unit has the Structure B. In some examples, the branching unit has the Structure C. In some examples, the copolymer includes branching units of Structure B and Structure C.

The branched $R^4$ groups are prepared from at least one tri-functional component. The tri-functional component provides the branching from the linear copolymer structure. The tri-functional component can be a component that includes three groups selected from the group consisting of hydroxyl groups, amine groups, and mixtures thereof. The tri-functional component can be, e.g., a triol (e.g., glycerin), a triamine, or a combination thereof. In some embodiments, the triamine can be a poly(alkylenoxy)triamine (e.g., JEFFAMINE T-403, a $C_6$ triamine substituted with oxypropylene groups and commercially available from Huntsman Chemical). Use of the triol to prepare the copolymers described herein provides the branched structure according to Structure B. In other words, glycerin or another suitable triol is included as a reactant to form the copolymer of Formula I where $R^4$ contains Structure B as a branching unit. Similarly, the triamine is included as a reactant to form the copolymer of Formula I where $R^4$ contains Structure C as a branching unit. In some embodiments, the $R^4$ groups are prepared from a combination of glycerin and a poly(alkylenoxy)triamine. In some embodiments, the triol is a poly (alkylenoxy)triol. In some embodiments, at least a portion of the branched $R^4$ groups are not alkoxylated (are not substituted with alkylene oxide groups). For example, in some embodiments, when the Y—$R^4$—Y is derived from a triol such as glycerin, the triol is not alkoxylated (e.g. glycerin is not alkoxylated). Alternatively, in some embodiments, when the Y—$R^4$—Y is derived from a triamine, it is not alkoxylated.

In addition to the tri-functional component, a portion of the $R^4$ groups can be incorporated into the copolymer through a diamine to produce $R^4$ groups that are not branched. In some examples, the diamine can be an alkylene diamine (i.e., a diamine of the formula $H_2N$—$R^4$—$NH_2$ where $R^4$ is a hydrocarbon) or a polyetherdiamine (i.e., a diamine of the formula $H_2N$—$R^4$—$NH_2$ wherein $R^4$ is a polyether).

Thus, the diamine may be an alkylene diamine having $R^4$ hydrocarbon groups as described herein. Exemplary alkylene diamines, most or all of which are commercially available include, without limitation, ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine. In one aspect, the diamine has the formula $H_2N$—$R^{11}$—$NH_2$ wherein $R^{11}$ is a $C_{2-6}$ hydrocarbon diradical.

In some examples, the diamine can be a polyetherdiamine, also referred to herein as a PAO (for polyalkyleneoxy)diamine. Polyetherdiamines can be obtained from Tomah Products, Inc. (Milton, Wis.), and Huntsman Chemical. A suitable polyetherdiamine is a poly(propyleneoxy)diamine, such as JEFFAMINE 230, JEFFAMINE D-400, JEFFAMINE D-2000, and XTJ-502 (formerly JEFFAMINE ED-2003), where each of these polyetherdiamines is commercially available from Huntsman Corporation (Salt Lake City, Utah). Another suitable diamine is a poly(ethyleneoxy)-co-propyleneoxy)diamine such as HUNTSMAN XTJ-500. Other suitable diamines include DPA-DEG, having the chemical structure $H_2N$—$CH_2CH_2CH_2$—O—$CH_2CH_2$—O—$CH_2CH_2$—O—$CH_2CH_2CH_2$—$NH_2$; and XTJ-504 (formerly JEFFAMINE EDR-148), which is also known as triethyleneglycoldiamine. In one embodiment, the polyetherdiamine has the structure $NH_2$—$CH(CH_3)CH_2O$—$(CH_2CHR'O)_x$—$CH_2CH(CH_3)$—$NH_2$, where R and R' are methyl or H. Huntsman also sells triethyleneglycol diamine under their XTJ-504 diamine designation (formerly JEFFAMINE EDR-148 diamine) having the structure $H_2N$—$CH_2CH_2$—O—$CH_2CH_2$—O—$CH_2CH_2$—$NH_2$, which may be used as the polyetherdiamine. Additional suitable polyetherdiamines from Huntsman include XTJ-511, having the structure $H_2N$—$C(CH_3)CH_2$—O—$CH_2CH_2$—O—$CH_2CH_2$—O—$CH_2C(CH_3)H$—$NH_2$; and XTJ-523 diamine having the structure $H_2N$—$C(CH_2CH_3)H$—$CH_2$—(O—C$(CH_2CH_3)H$—$CH_2)_a$—$OCH_2C(CH_2CH_3)$—$NH_2$ where a is approximately 26. In some embodiments, the diamine is ethylene diamine. The diamine can be used in amounts of 50% or less, 40% or less, 30% or less, or 20% or less based on the total amount of difunctional and trifunctional amines and alcohols present, on an equivalents basis.

The polyether polyamide block copolymers described herein can have an acid number of less than 25, less than 20, less than 15, or less than 10. Since the copolymer does not have any free carboxylic acid groups, the copolymer should theoretically have an acid number of zero. However, when prepared from dibasic acid, a $C_2$-$C_{12}$ aliphatic diamine, a monofunctional poly(alkyleneoxy)monoamine, and a trifunctional component according to a process described herein, some of the diacid may not react. Thus, the resulting final product can have some unreacted carboxylic acid which would result in the copolymer having an acid number greater than zero. In some examples, the amount of unreacted diacid is minor. Therefore, the copolymer can have a small acid number. Esterification catalysts can optionally be used to encourage all of the diacid to react with hydroxyl groups, so as to minimize the amount of free acid, i.e., to reduce the acid number of the product.

The polyether polyamide block copolymers described herein can have an amine number of less than 25, less than 20, less than 15, less than 10, less than 5, less than 2, or less than 1. Since the copolymer does not have any free amine groups, the copolymer should theoretically have an amine number of zero. However, some of the amine containing starting materials may not react, thus leaving unreacted amine in the product. In some examples, the amount of unreacted amine is minor and the resulting copolymer has a small amine number. Amidification catalysts can be used to encourage all of the diamine to react with carboxyl groups, so as to minimize the amount of free amine, i.e., to reduce the amine number of the product.

The polyether polyamide block copolymers described herein, and compositions containing these copolymers, can have a softening point of from 60 to 140° C. (Ring and Ball, or Mettler). For example, the softening point can be from 75 to 125° C. or 85 to 100° C.

The polyether polyamide block copolymers described herein, and compositions containing these copolymers, can have a weight or number average molecular weight from 5,000 to 30,000. The molecular weight can be measured by preparing a solution of the copolymer or composition in a suitable solvent, e.g., tetrahydrofuran (THF) and identifying the retention time of the copolymer by gel permeation chromatography, and comparing that retention time to the retention times of solutions of polystyrene having known molecular weight characterizations. In one aspect, the copolymers have a weight or number average molecular weight of greater than 5,000. In another aspect, the copolymer have a weight average molecular weight of less than 30,000. In other aspects, the copolymers have a weight average molecular weight in the range of 6,000 to 25,000; 10,000 to 20,000; and 15,000 to 20,000. The molecular weight can be controlled by controlling the relative amounts of monofunctional, difunctional and trifunctional reactants used and the molecular weight of the reactants used (including the amount of alkoxylation of the particular reactants). Among other features, the hydrocarbon termination on the polyether reactant allows for control of the molecular weight of the copolymer.

In some examples, the polyether polyamide block copolymers and compositions can have a viscosity, as measured on the neat copolymer or composition at 160° C., of less than 5,000 centipoise (cPs or cps). For example, the viscosity can be less than 4,000 cPs, less than 3,000 cPs, less than 2,000 cPs, or less than 1,000 cPs. In some examples, the copolymer and compositions can have a melt viscosity, as measured on the neat copolymer or composition at 160° C., of more than 50 cPs (e.g., more than 500 cPs).

As described herein, the polyether polyamide block copolymers are prepared by mixing a dibasic acid, a $C_2$-$C_{12}$ aliphatic diamine (i.e., a short-chained aliphatic diamine), a monofunctional poly(alkyleneoxy)monoamine, and a trifunctional component selected from the group of triols, poly(alkyleneoxy)triamines, and mixtures of these. The starting materials can be reacted together with a stoichiometry, and under reaction conditions, such that the acid number of the resulting block copolymer is less than 25, less than 15, or less than 10, while the amine number is less than 10, less than 5, or less than 1. The softening point of the polyether polyamide block copolymer is preferably greater than room temperature (e.g., from 50° C. to 150° C. or from 75° C. to 125° C.).

Controlling the stoichiometry of the reactants can be important in preparing the polyether polyamide block copolymers described herein. As used herein, "equivalents" refers to the number of reactive (functional) groups present in a molar quantity of a molecule, such that a mole of a dicarboxylic acid (e.g., sebacic acid) has two equivalents of carboxylic acid, while a mole of monoamine has one equivalent of amine. In some examples, the diacid used to prepare the polyether polyamide block copolymers described herein has only two reactive groups (both carboxylic acids, although dimer acid can contain a small amount of tricarboxylic acid) and the diamine has only two reactive groups (both primary amines).

In some embodiments, when co-diacid is used to prepare a block copolymer, the co-diacid contributes up to 50% of the equivalents of carboxylic acid present in the reaction mixture. Stated another way, the co-diacid contributes from 0-50 equivalent percent of the acid equivalents in the reaction mixture. For example, the co-diacid can contribute 0-30 equivalent percent or 0-10 equivalent percent of the acid equivalents in the reaction mixture.

The stoichiometry of the reactants can have a significant impact on the composition of the polyether polyamide block copolymer. For example, copolymers made with increasing amounts of polyether will tend to have lower (number and weight) average molecular weights. On the other hand, as less polyether is used, the average molecular weight of the molecules that comprise the block copolymer will increase. In some examples, the equivalents of carboxylic acid are substantially equal to the combined equivalents of hydroxyl- and amine-functional components. In some examples, the amount of the dibasic acid present during the reaction is from 40% to 50% by weight of the total reactants present.

In general, increasing the average molecular weight of the copolymer will tend to increase the melting point and melt viscosity of the copolymer. When a high melting point copolymer is combined with a polar liquid to thereby form a gel, the gel will tend to have a firmer consistency than does a gel formed from a copolymer with a low melting point.

In order to prepare a block copolymer of the present invention, the above-described reactants (the dibasic acid, $C_2$-$C_{12}$ aliphatic diamine (i.e., a short-chained aliphatic diamine), monofunctional monoamine, and tri-functional component including three groups selected from the group of hydroxyls, amines, and mixtures of these) can be combined in any order. In one embodiment, the reactants are mixed together and heated for a time and at a temperature sufficient to achieve essentially complete reaction, to thereby form the block copolymer. The terms "complete reaction" and "reaction equilibrium" as used herein have essentially the same meaning, which is that further heating of the product does not result in any appreciable change in the acid or amine numbers of the copolymer.

Thus, the polyether polyamide block copolymers can be formed in a one-step procedure, wherein all of the components are combined and then heated to about 200-250° C. for a few hours (e.g., 2-8 hours). In some examples, when lower temperatures are used, a longer reaction time is needed to achieve complete reaction. However, when the reaction temperature is too high, the reactants and/or products can undergo undesirable thermally-induced decomposition. The reactants can be exposed to a temperature in excess of 100° C. to drive off the water formed by the condensation of the reactants. Since one or more of the reactants can be a solid at room temperature, it can be convenient to combine each of the ingredients at a slightly elevated temperature, and then form a homogeneous mixture prior to heating the reaction mixture to a temperature sufficient to cause reaction between the components. Alternatively, two of the reactants can be combined and reacted together, and then the remaining reactants can be added simultaneously or sequentially, followed by further heating, until the desired product is obtained. Reaction progress can be monitored by periodically measuring the acid and/or amine number of the product mixture.

Catalysts that can accelerate amide and/or ester formation can be present in the reaction mixture described above. Thus, mineral acid such as phosphoric acid, or tin compounds such as dibutyltin oxide, can be present during the reaction. In addition, it is preferred to remove water from the reaction mixture as it is formed upon amide and ester formation. Water removal can be accomplished by maintaining a vacuum on the reacting mixture, or by passing a stream of an inert gas (e.g., nitrogen) across the top of the reaction mixture.

The block copolymers described herein can be used to thicken and/or gel a liquid or a mixture of liquids. As used herein, the term liquid refers to any substance that is or can be a liquid (as opposed to a solid or gas) at a temperature between 10-60° C. Generally stated, a liquid is a fluid material where the components of the material are held together by intermolecular interactions, as opposed to a gas, where a gas is also fluid but the components of the gas are not held together by intermolecular interactions. A material described herein is a "liquid" even though under a specific set of conditions the material does not flow. For example, methyl ethyl ketone (MEK), also known as 2-butanone, is a liquid according to the present description even though MEK can be a solid under certain conditions (e.g., at less than −87° C.) and can be a gas under other conditions (e.g., at greater than 80° C.). Thus, a composition as described herein that includes a "liquid" does not necessarily have that liquid in a fluid state. For example, a composition of the present invention that contains MEK is still a composition as described herein even though the composition may be at such a low temperature that the liquid no longer flows, and in fact may be regarded as a solid. As long as the candidate liquid in neat form is capable of flowing at a temperature between 10-60° C., then it is a liquid according to the present description.

The compositions described herein can be a liquid, for example, at elevated temperatures. The composition can alternatively be a gel, for example, at room temperature (e.g., at 25° C.). Even when the composition is in the gel state, as explained above, the polar liquid of the composition will be deemed to be a "liquid", i.e., a fluid, so long as the polar liquid in a neat state would be a liquid at at least one temperature in the range of 10-60° C. The polar liquid need not be fluid in the composition, e.g., the composition need not, and preferably does not demonstrate syneresis.

The liquid present in the compositions described herein is not only fluid at at least one temperature in the range of 10-60° C., but it is also polar. The term "polar" refers to a liquid containing a dipole moment. In one embodiment, the liquid contains a heteroatom, e.g., oxygen or nitrogen, in addition to one or more carbons, where the presence of the heteroatom will typically imbue the liquid with a dipole so that the liquid is a polar liquid. For example, the polar liquid can contain one or more oxygen atoms, and be a ketone-containing liquid, an ester-containing liquid, or an ether-containing polar liquid. The polar liquid can contain oxygen and nitrogen atoms, e.g., the polar liquid can be an amide-containing liquid. In some examples, the polar liquid can contain oxygen and sulfur atoms, e.g., the polar liquid can be a sulfoxide-containing liquid.

In one embodiment, the polar liquid or surfactant forms a gel upon being combined with a poly/ether polyamide block copolymer as described herein. For example, the polar liquid can be an ester-containing liquid having a formula selected from $R^6$—$CO_2$—$R^6$ and $R^6$—$CO_2$—$R^7$—$CO_2$—$R^6$ wherein $R^6$ and $R^7$ are organic moieties having 1-12 carbons, where two $R^6$ moieties in a liquid can be joined together to provide a lactone, and a $R^6$ and $R^7$ moiety in a liquid may be joined together to form a lactone. For example, $R^6$ may be selected from $C_1$-$C_{12}$ alkyl, $C_1$-$C_{12}$ hydroxy-substituted $C_1$-$C_{12}$ alkyl, $C_1$-$C_{12}$ alkoxy-substituted $C_1$-$C_{12}$ alkyl, $C_6$-$C_{12}$ aryl-substituted $C_1$-$C_{12}$ alkyl, $C_1$-$C_{12}$ alkenyl, $C_1$-$C_{12}$ hydroxy-alkenyl, $C_1$-$C_{12}$ alkoxy-substituted $C_1$-$C_{12}$ alkenyl, $C_6$-$C_{12}$ aryl, $C_1$-$C_{12}$ alkyl-substituted $C_6$-$C_{12}$ aryl, $C_6$-$C_{12}$ hydroxy-substituted aryl, $C_6$-$C_{12}$ alkoxy-substituted $C_6$-$C_{12}$ aryl; and $R_7$ may be selected from $C_1$-$C_{12}$ alkylene, $C_1$-$C_{12}$ hydroxy-substituted alkylene, $C_2$-$C_{12}$ alkenylene, $C_6$-$C_{12}$ arylene, $C_6$-$C_{12}$ hydroxy-substituted $C_6$-$C_{12}$ arylene, $C_1$-$C_{12}$ alkoxy-substituted $C_6$-$C_{12}$ arylene. As another example, the ester-containing liquid can be selected from the group consisting of ethyl lactate, butyl propionate, dibutyl adipate, ethoxyethyl propionate, butyl acrylate, vinyl propionate, butyl acetate, dibutyl sebacate, diethylphthalate, vinyl acetate, methyl methacrylate, ethyl acetate, ethyl hexyl acetate, and gamma-butyrolactone.

In some examples, the polar liquid can be an aromatic liquid. For example, the aromatic liquid can be selected from the group consisting of benzene, toluene, o-xylene, m-xylene, p-xylene, styrene, alpha-methyl styrene, ($C_1$-$C_{18}$ alkyl) benzoate, ($C_1$-$C_{18}$ alkyl)salicylate, and ($C_1$-$C_{12}$ alkyl)($C_1$-$C_{12}$ alkyl)phthalate. In some examples, the polar liquid is 2-ethylhexy salicylate, an alkyl benzoate, or benzyl benzoate. In some examples, the polar liquid can be a polar aprotic liquid. For example, the polar aprotic liquid can be selected from the group consisting of N-methyl pyrrolidinone, propylene carbonate, tetrahydrofuran, dimethyl sulfoxide, methylene chloride, and dichloroethane.

The polar liquid can optionally be a ketone-containing liquid. For example, the ketone-containing liquid can have the formula $R^6$—C(=O)—$R^6$ wherein $R^6$ at each occurrence is independently selected from organic moieties having 1-12 carbons. In some examples, two $R^6$ moieties in a liquid can be joined together to provide a cyclic ketone. The ketone-containing polar liquid can be, for example, acetone, methyl ethyl ketone, methyl isobutyl ketone, or cyclohexanone. In some examples, the polar liquid is a sulfoxide-containing liquid. For example, the sulfoxide-containing liquid can have the formula $R^8$—(S=O)—$R^8$ and $R^8$ is independently selected at each occurrence from $C_1$-$C_6$ alkyl. In other examples, the polar liquid can be a glycol ether. For example, the polar liquid can be a glycol ether of the formula $R^9$—[O—$R^{10}$-]$_n$—OH wherein $R^9$ is a $C_1$-$C_{22}$ hydrocarbon, $R^{10}$ is a $C_2$-$C_6$ hydrocarbon independently selected at each occurrence, and n is an integer selected from 1, 2, 3, 4, 5 and 6. Alternatively, the glycol ether can be ethyleneglycol mono phenyl ether, dipropyleneglycol mono methyl ether, or tripropyleneglycol mono methyl ether.

Further examples of polar liquids that can be used in the compositions described herein include commercially available polar liquids as known in the art. The polar liquids can be obtained, for example, from Acros Organics (Pittsburgh, Pa.), Aldrich Chemical (Milwaukee, Wis.; including Sigma Chemical and Fluka), Apin Chemicals Ltd. (Milton Park, U.K.), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Chemical Company (Kingsport, Tenn.), Eastman Kodak Company (Rochester, N.Y.), Fisher Scientific Co. (Pittsburgh Pa.), Fisons Chemicals (Leicestershire, U.K.), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Company (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), and Wako Chemicals, Inc. (Richmond, Va.).

In another example, the polar liquid can include a liquid fragrance (i.e., an aroma chemical or a fragrance oil). Liquid fragrances are well known in the art and are sold by many companies. The liquid fragrances suitable for use in the compositions described herein can be obtained from IFF (New York, N.Y.); Givaudan (Vernier, Switzerland); Firmenich (Princeton, N.J.); Quest International (Naarden, The Netherlands); Takasago (Rockleigh, N.J.); Haarman & Reimer (Holzminden, Lower Saxony, Germany); Dragoco (Holzminden, Lower Saxony, Germany); T. Hasegawa Co., Ltd. (Tokyo, Japan); Mane SA (Bar-sur-Loup, France); Aldrich-Sigma Flavors and Fragrances, a group within Aldrich Chemical Co., Inc. (Milwaukee, Wis.).

Fragrance chemicals can be classified based upon their functional groups. Classes of fragrance chemicals include, for example, acetylenes, alcohols, aldehydes, amines, amino acids, carboxylic acids, essential oils, ester/lactones, ethers/acetals, heterocycles, hydrocarbons, ketones, nitriles, olefins (including cumulated double bonds), and sulfur compounds (sulfides, disulfides and mercaptans). Fragrance chemicals can also be classified based on their scent. For example, aliaceous, animal, balsamic, camphoraceous, citrus, coffee, earthy, ethereal, floral, fruity, green, herbaceous, meaty, medicinal, minty, mossy, musty, nutty, pepper, smoky, soapy, spicy, sulfurous, vegetable, waxy, wine-like, and woody are common scents that are recognized by aroma chemists. These classes of fragrance chemicals represent fragrance chemicals as described herein. Essential oils, which are naturally-derived fragrance chemicals, are also liquid fragrances as described herein.

The combination of a composition comprising a polyether polyamide block copolymer as described herein and a liquid fragrance chemical or fragrance oil can be utilized as a fragrance-emitting article. In order to formulate a fragrance-emitting article from the composition described herein, blends of fragrance oil and the block copolymer can be prepared at various weight ratios, e.g., 10%, 20%, 30%, 40%, 50%, 60%, 70%, 80%, and 90% by weight of fragrance oil in a mixture containing the fragrance oil and block copolymer. In some embodiments, these blends can be heated to provide a homogeneous composition, and then cooled to provide the fragrance-emitting article. The formulator can select a suitable formulation that meets the needs of consistency and fragrance-release characteristics for the desired end-use. When gel-like consistencies are created, the gel can be molded into various shapes. Other components can be added to the compositions, to provide desirable end-use properties in addition to fragrance release.

In another embodiment, the polar liquid can include a liquid polyepoxy resin. The liquid polyepoxy resins suitable for use in the compositions described herein include any liquid organic compound having at least two oxirane rings (i.e., epoxy groups). In addition to the epoxy groups, the polyepoxy resin can contain aliphatic, alicyclic, heterocyclic, cycloaliphatic, aromatic groups, and combinations of these. The polyepoxides can be linear polymers having terminal epoxy groups (e.g., a diglycidyl ether of a polyoxyalkylene glycol), polymers having skeletal oxirane units (e.g., a polybutadiene polyepoxide), or polymers having pendent epoxy groups (e.g., a glycidyl methacrylate polymer or copolymer). The molecular weights of the liquid polyepoxy resins can vary from about $10^2$ to about $10^5$ or more. Mixtures of various epoxy resins can also be used in the hot melt compositions described herein.

Examples of liquid polyepoxy resins are described in U.S. Pat. Nos. 3,117,099 and 3,018,262. Specific examples of polyepoxy resins include halogenated epoxy resins; 1,4-butanediol diglycidyl ether (e.g., ARALDITE RD-2; Ciba-Geigy Corp.; Hawthorne, N.Y.); diglycidyl ethers of bisphenol A (e.g., EPON 828, EPON 1004, and EPON 1001F, all commercially available from Resolution Performance Products, Inc. (Houston, Tex.); and DER-332 and DER-334 from Dow Chemical Co., Midland, Mich.); diglycidyl ether of bisphenol F (e.g., ARALDITE GY281 from Ciba-Geigy Corp., Hawthorne, N.Y., and EPON 862 from Resolution Performance Products, Inc.); 3,4-epoxycyclohexyl-methyl-3,4-epoxycyclohexene carboxylates (e.g., ERL-4221 from Dow Chemical Company); vinylcyclohexene dioxide (e.g., ERL 4206 from Dow Chemical Co.); bis(3,4-epoxycyclohexyl) adipate (e.g., ERL-4299 from Dow Chemical Co.); dipentene dioxide (e.g., ERL-4269 from Dow Chemical Company); epoxidized polybutadiene (e.g., OXIRON 2001 from FMC Corp., Philadelphia, Pa.); 2-(3,4-epoxycyclohexyl-5,5-spiro-3,4-epoxy)cyclohexane-metadioxane (e.g., ERL-4234 from Dow Chemical Company); epoxysilanes, e.g., beta-3,4-epoxycyclohexylethyltrimethoxysilane and gamma-glycidoxypropyltrimethoxysilane; hydrogenated bisphenol A-epichlorohydrin based epoxy resins (e.g., EPONEX 1510 from Resolution Performance Products, Inc.); and polyglycidyl ethers of phenolformaldehyde novolaks (e.g., DEN-431 and DEN-438 from Dow Chemical Co.).

The combination of a composition comprising a polyether polyamide block copolymer as described herein and a liquid polyepoxy resin, can be utilized in, e.g., preparing structural materials. Polyepoxides can be cured by various materials well known in the art, e.g., amines, to form a crosslinked structure. This crosslinking structure can take many shapes, e.g., a film. The film can be used as a top coat for a coated substrate, where the film provides effective barrier properties that allows the coated substrate to retain desirable properties for longer periods of time. Cured epoxy resin can also be used as an adhesive composition.

To determine a suitable formulation for a composition comprising a polyether polyamide block copolymer as described herein and a liquid polyepoxy resin, the two components can be combined in various weight ratios. For example, blends of liquid polyepoxy resin and polyether polyamide block copolymer-containing compositions can be prepared at various weight ratios, e.g., 5%, 10%, 20%, 30%, 40%, 50%, 60%, 70%, 80%, and 90% by weight of liquid polyepoxy resin in a combination of polyepoxy resin and polyether polyamide block copolymer. These blends can be heated to provide a homogeneous composition, and then cooled to room temperature. The formulator can select from these formulations a suitable formulation that meets the needs of consistency and reactivity with curing agents, for the desired end-use. When gel-like consistencies are created, the gel can be molded into various shapes. Other components can be added to the compositions to provide desirable end-use properties in addition to structural and adhesive properties.

In some examples, the compositions described herein can be combined with a surfactant, such as, for example, a liquid surfactant. The term "surfactant" includes soaps and detergents. Surfactants suitable for use in the compositions described herein include anionic, cationic, zwitterionic, and nonionic surfactants. Examples of suitable nonionic surfactants for use in the compositions described herein include surfactants containing an ester bond, such as glycol esters of fatty acids, glycerol esters of fatty acids, polyglycerol esters of fatty acids, tetritol, pentitol and hexitol esters of fatty acids, polyethylene glycol esters of fatty acids, sucrose esters of fatty acids, sucrose esters of triglycerides, sorbitan esters of fatty acids, and polyoxyethylenated sorbitan esters or polysorbates. The nonionic surfactants can optionally contain an ether bond, such as polyoxyethylene glycol alkylphenyl ethers and polyoxyethylene glycol fatty alkyl ethers. The nonionic surfactants can optionally contain an amide bond, e.g., polyoxyethylenated alkylamides and alkylene oxide copolymers. Many nonionic surfactants are liquid at room temperature and are thus readily incorporated into the compositions described herein.

Exemplary cationic or zwitterionic surfactants include betaines, such as decyl betaine, lauryl betaine, lauramidopropyl betaine, myristyl betaine, myristamidopropyl betaine, coco-betaine, cocoamidoethyl betaine, cocoamidopropyl betaine, cetyl betaine, palmamidopropyl betaine, palmitamidopropyl betaine, ricinoleamidopropyl betaine, stearamidopropyl betaine, stearyl betaine, oleyl betaine, oleamidopropyl betaine, and behenyl betaine. Further examples of cationic or zwitterionic surfactants include the sultaines, such as lauryl sultaine, lauryl hydroxysultaine, coco-sultaine, coco-hydroxysultaine, cocoamidopropyl hydroxysultaine, and oleamidopropyl hydroxysultaine. Alkyltrimethylammonium salts are other examples of cationic surfactants. Representative examples include dodecyltrimethylammonium bromide or chloride; cocotrimethylammonium chloride; cetyltrimethylammonium chloride, bromide, methosulphate, or tosylate; (hydrogenated)trimethylammonium tallow chloride; stearyltrimethylammonium chloride; octyldodecyltrimethylammonium chloride; behenyltrimethylammonium chloride or methosulphate; benzalkonium chloride, bromide or saccharinate; cetalkonium chloride; cetearalkonium bromide; lauralkonium chloride or bromide; stearalkonium chloride; olealkonium chloride; behenalkonium chloride; and cocoylbenzylhydroxyethylimidazolinium chloride. Examples of anionic surfactants include soaps and carboxylate and sulfonate salts, e.g., fatty acid salts including sodium or potassium or other suitable counterion.

To determine a suitable formulation for a composition comprising a polyether polyamide block copolymer as described herein and surfactant, the two components can be combined in various weight ratios. For example, blends of surfactant and polyether polyamide block copolymer-containing compositions can be prepared at various weight ratios, e.g., 5%, 10%, 20%, 30%, 40%, 50%, 60%, 70%, 80%, and 90% by weight of surfactant in a combination of surfactant and polyether polyamide block copolymer-containing resin. These blends can be heated to provide a homogeneous composition, and then cooled to room temperature. The formulator can select from these formulations a suitable formulation that meets the needs of consistency and surfactancy. When gel-like consistencies are created, the gel can be molded into various shapes. Other components can be added to the compositions to provide desirable end-use properties in addition to surfactancy properties. These compositions can be used in, for example, cosmetics and cleaning compositions.

The polyether polyamide block copolymer and polar liquid can be combined so as to provide a mixture that has a gel-like consistency. In general, materials that have a gel-like character can maintain their shape when undisturbed but flow upon being rubbed. Gels prepared with block copolymers of the present invention can be anywhere from soft to hard, where a "hard" gel has a rigid structure and is very resistant to deformation, while a "soft" gel exhibits some, but not too much, resistance to deformation. An illustration of "soft" gel can be seen in the preparation of JELL-O dessert, which is a well known food product from Kraft Foods Inc. (division of Philip Morris Companies Inc.; Northfield, Ill.). When prepared according to the package instructions, JELL-O dessert is mixed with water to form a relatively soft gel. A gellant may be distinguished from a rheological additive, where a rheological additive increases the shear thinning of a polar liquid/additive combination, while a gellant imparts a solid phase to the polar liquid/gellant combination. In one embodiment, the block copolymer described herein is not a rheological additive. In one aspect, the composition can be a gel composition comprising the polyether polyamide block copolymer and a suitable polar liquid.

In some embodiments, the polar liquid is a liquid at room temperature or slightly above room temperature. A preferred polar liquid is a polar solvent, where exemplary polar solvents include lower alcohols (e.g., methanol, ethanol, propanol, and butanol), glycols, ethers, glycol ethers (i.e., polyalkyleneglycol ethers), and polyols. The polar solvent can be a mixture of solvents. Exemplary polar solvents are described in Table B. DOWANOL E-200 and &300 are two exemplary polyethylene glycols from the DOWANOL family of glycol ethers from Dow (Midland, Mich.). DESMOPHEN 550 U and 1600 U are polyether polyols from the DESMOPHEN family of products commercially available from Bayer Corporation (Pittsburgh, Pa.).

TABLE B

Polar Liquids Coataining Hydroxyl and/or Ether Functionalities

| Name | CAS | Structure | Functionality |
|---|---|---|---|
| Hexylene glycol (a.k.a. 2-methyl-2,4-pentandiol) | 107-41-5 | $CH_3CH(OH)CH_2C(CH_3)_2OH$ | 1 secondary OH<br>1 tertiary OH |
| Propylene glycol (a.k.a. 1,2-propanediol) | 57-55-6 | $CH_3CH(OH)CH_2OH$ | 1 primary OH<br>1 secondary OH |
| Ethylene glycol | 107-21-1 | $HOCH_2CH_2OH$ | 2 primary OH |
| Di(propylene glycol) Mixture of 1,2 and 1,3 isomers | 25265-71-8 | $HOC_3H_6OC_3H_6OH$ | 2 primary OH's<br>2 secondary OH's<br>1/1 prim/sec OH<br>1 ether |
| Di(ethylene glycol) ethyl ether | 111-90-0 | $C_2H_3OCH_2CH_2OCH_2CH_2OH$ | 2 ether<br>1 prim. OH |
| Diethylene glycol dimethyl ether (a.k.a. 2-methoxyethyl ether) | 111-96-6 | $CH_3OCH_2CH_2OCH_2CH_2OCH_3$ | 3 ether |
| DOWANOL ™ T34 E-200 Poly(ethylene glycol) MW = 200 | 25322-68-3 | $H(OCH_2CH_2)_nOH$ | 2 prim. OH<br>~4 ether |
| DOWANOL ™ E-300 Poly(ethylene glycol) MW = 300 | 25322-68-3 | $H(OCH_2CH_2)_nOH$ | 2 prim. OH<br>6 ether |
| DESMOPHEN ™ 1600 U Linear polyether polyol | 25322-69-4 | NOT KNOWN | NOT KNOWN |
| DESMOPHEN ™ 550 U Branched polyether polyol | 25723-16-4 | NOT KNOWN | NOT KNOWN |
| Poly(ethylene glycol) dimethyl ether MW = 250 | 24991-55-7 | $CH_3(OCH_2CH_2)_nOCH_3$ | ~6 ether |

In one aspect, the polar liquid is a liquid that contains ether and/or hydroxyl groups. For example, the polar liquid can be dimethylsulfoxide (DMSO). The liquid can contain more than one component, e.g., the liquid can be an ether-containing material as well as a hydroxyl-containing material. In the mixture, the gellant (i.e., the polyether polyamide block copolymer) typically contributes 10-95%, and the polar liquid typically contributes 5-90%, of the combined weight of the gellant and the polar liquid. In some embodiments, the gellant is combined with the polar liquid such that the weight percent of gellant in the gellant+polar liquid mixture is from 5-50% (e.g., from 1045%). Such mixtures can be gels, where the gels can be transparent, translucent, or opaque, depending on the precise identities of the gellant and polar liquid, as well as the concentration of gellant in the mixture.

To prepare a gel from a polar liquid and a polyether polyamide block copolymer, the two components are mixed together and heated until the copolymer is substantially dissolved in the liquid medium (i.e., until the mixture is homogeneous). A temperature within the range of from 80° C. to 140° C. is typically sufficient to allow the block copolymer to completely dissolve in the polar liquid. A lower temperature can be used if a solution can be prepared at the lower temperature. Upon cooling to ambient temperature, the mixture forms the gelled composition. Optional components can be added to the molten composition and dispersed and/or dissolved to provide a homogeneous composition prior to cooling of the molten composition.

In another embodiment, the polyether polyamide block copolymer-containing gels described herein can be formulated such that they are transparent. The gels described herein can have various degrees of transparency, ranging from "crystal" clear to hazy. The absolute transparency of the gel can be measured by determining the percent haze of the gel according to the following method. A white light is shined through a gel sample of a given thickness at room temperature, and the diffuse transmittance and the total transmittance of the light are determined. The percent haze for a sample is determined by the equation: % haze=(diffuse transmittance/total transmittance)×100. Samples are prepared by melting the gel (or product made therefrom) and pouring the melt into 50 mm diameter molds. The samples can be prepared at two thicknesses, e.g., 5.5±0.4 mm and 2.3±0.2 mm.

Clarity measurements can be made on a Hunter Lab Ultrascan Sphere Spectrocolorimeter using the following settings: specular included, UV off, large area of view, illuminate D65, and observer 10°. Using this protocol with a 2.3 mm thickness sample, the polyether polyamide block copolymer-containing gel described herein can have, for example, a % haze value of less than 75%. In comparison, paraffin wax has a % haze value of over 90%. The % haze value for a gel described herein can be increased if desired, by appropriate selection of polar liquid and gellant. Thus, the methods described herein provide gels (and articles made therefrom) having a transparency (measured by % haze) of less than 75%. For example, the % haze can be less than 50%, less than 25%, less than 10%, or 5% or less.

In one embodiment, the gels containing polyether polyamide block copolymers are stable, in that they do not display syneresis. Syneresis refers to the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, synersis is typically an undesirable property, and the gels described herein do not exhibit syneresis. In one embodiment, the articles prepared from the gels are stable in that they do not exhibit syneresis. Thus, the articles do not have an oily feeling when handled.

The compositions including the polyether polyamide block copolymers and the polar liquid can be used to prepare controlled release products. As used herein, "controlled release products" refers to products that modulate the release of an active agent from the formulation. In some examples, the controlled release products include a bio-active solid or liquid component dissolved in the polar liquid. The bio-active solid or liquid can be any solid or liquid that imparts a function upon the resultant composition and/or article a function. In some examples, the active solid is a semi-solid. In some examples, the active liquid is a volatile or non-volatile organic liquid. The active liquid can further be a semi-solid or a solid dissolved in a carrier liquid (e.g., a diluent). In some examples, the active liquid can include or consist of water and an active agent dissolved in the water. Alternatively, the active liquid can include or consist of an organic liquid and an active agent dissolved in the liquid. Examples of suitable bio-active solids and liquids include therapeutic active solids and liquids, nutraceutical active solids and liquids, cosmeceutical active solids and liquids, pesticidal active solids and liquids, laundry care active solids and liquids, fragrance oils, surface treating chemicals, radio-tracers, surfactants, or a mixture of these.

Examples of active ingredients contained in the bio-active solid or liquid can be therapeutically active ingredients (for humans or animals) such as medicines, drugs, pharmaceuticals, bioceuticals which are optionally combined with a biologically-acceptable carrier. Further, examples of the active ingredient contained in the bio-active solid or liquid can be biological compound such as amino acids, vitamins, carbohydrates, and/or steroids. Examples of biological compounds include biopolymers, biocopolymers, or chimera comprising DNA, RNA, oligonucleotides, modified DNA, modified RNA, proteins, polypeptides, and modified polypeptides.

The compositions including the polyether polyamide block copolymers and the polar liquid can be included in personal care products. These personal care products can further include a cosmetically or dermatologically active compound. Exemplary active compounds include anti-acne agents, anti-inflammatory agents, anti-irritants, antioxidants, radical scavengers, and mixtures thereof suitable for use in cosmetics. Further examples of active compounds include vitamins A, B3, B5, B6, B8, C, E, or PP, niacin, carotenoids (e.g., β-carotene, lycopene, astaxanthin, zeaxanthin, lutein, and flavonoids such as catechins, hesperidin, proanthocyanidins and anthocyanins), polyphenols, and minerals (e.g., zinc, calcium, and magnesium). One or more prebiotics can also be included in the compositions described herein. Suitable prebiotics include, for example, oligosaccharides produced from glucose, galactose, xylose, maltose, sucrose, lactose, starch, xylan, hemicellulose, inulin, gums of acacia type, or mixtures of these. Active substances for use in the compositions described herein further include anti-cellulite agents, tanning agents, skin lightening agents, skin soothing agents, skin healing agents, antimicrobial agents, and antifungal agents.

Ultraviolet (UV) radiation absorbing substances, including UV filters such as UVA and UVB filters, are also useful in the compositions described herein. The UVA and UVB filters can be soluble in water or oil. Examples of oil-soluble UVA filters include triazines and triazoles. An example of a water-soluble UVA filter for used with the compositions described herein is 2'-bis(1,4-phenylene)-1H-benzimidazole-4,6-disulfonic acid sodium salt.

Oil-soluble UVB filters according to the present invention include 3-benzylidenecamphor derivatives, 4-aminobenzoic acid derivatives, cinnamic acid esters, salicylic acid esters, benzophenone derivatives, benzalmalonic acid esters, 2-cyano-3,3-diphenylacrylic acid esters, diethylhexyl-butamidotriazone, and 2,4,6-trianilino-(p-carbo-2'-ethyl-1'-hexyloxy)-1,3,5-triazine. Water-soluble UVB filters include, for example, 2-phenylbenzimidazole-5-sulfonic acid and salts thereof, sulfonic acid derivatives of benzophenones, and sulfonic acid derivatives of 3-benzylidene camphor.

Active substances for use in the compositions described herein also include hydrophilic and lipophilic substances. Hydrophilic active substances of proteins or protein hydrolysates, amino acids, polyols (e.g., glycerol, sorbitol, butylene glycol and polyethylene glycol), urea and derivatives (e.g., hydroxyalkylurea derivatives), allantoin, sugars and sugar derivatives, starch, or bacterial or plant extracts (e.g., aloe vera extracts) can also be included in the compositions described herein. Suitable lipophilic active substances include some of the active substances mentioned above including retinol (vitamin A) and derivatives and tocopherol (vitamin E) and derivatives, and also includes ceramides, essential oils, and nonsaponifiable materials (e.g., tocotrienol, sesamin, γ-oryzanol, phytosterols such as stigmasterol, β-sitosterol, and campesterol, squalenes, waxes, or terpenes).

Moisturizing active substances can also be used in the compositions described herein. Examples include sphingoid-based compounds, glycosphingolipids, phospholipids, essential fatty acids, 1-2-diacylglycerol, 4-chromanone, pentacyclic triterpenes, petrolatum, hyaluronic acid and derivatives, pentanediol, pidolates, serine, xylitol, lactic acid, sodium lactate, glyceryl polyacrylate, ectoine and derivatives, chitosan, oligo- and polysaccharides, cyclic carbonates, N-lauroylpyrrolidonecarboxylic acid, N-α-benzoyl-L-arginine, and steroidal derivatives (e.g., DHEA).

The compositions described herein can be emulsions of a liquid or a semi-liquid. The emulsions can be obtained by dispersing an oil phase into an aqueous phase to form an oil in water (O/W) emulsion. Alternatively, the emulsions can be obtained by dispersing an aqueous phase into an oil phase to form a water in oil (W/O) emulsion. Other suitable emulsion types include, for example, cream emulsions and microemulsions. The oils, emulsifiers, and coemulsifiers for use in the emulsified compositions can be chosen by those of skill in the art.

Suitable emulsifiers for use in the compositions described herein include polyglyceryl-2 dipolyhydroxystearate, PEG-30 dipolyhydroxystearate, cetyldimethicone copolyol, glycol distearate, glycol dilaurate, diethylene glycol dilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, glyceryl stearate, glyceryl diisostearate, pentaerythrityl monooleate, sorbitan sesquioleate, isostearyl diglyceryl succinate, glyceryl caprate, palm glycerides, cholesterol and derivatives, lanolin, glyceryl oleate (containing 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20, sorbitan stearate, PEG-7 hydrogenated castor oil, PEG-5 soya sterol, PEG-6 sorbitan beeswax, glyceryl stearate SE, methylglucose sesquistearate, PEG-10 hydrogenated castor oil, sorbitan palmitate. PEG-22/dodecyl glycol copolymer, polyglyceryl-2 PEG-4 stearate, sorbitan laurate, PEG-4 laurate, polysorbate 61, polysorbate 81, polysorbate 65, polysorbate 80, triceteareth-4 phosphate, triceteareth-4 phosphate and sodium $C_{17-17}$-alkyl sec sulfonate, glyceryl stearate and PEG-100 stearate, polysorbate 85, trilaureth-4 phosphate, PEG-35 castor oil, sucrose stearate, trioleth-8 phosphate, $C_{12-15}$-Pareth-12, PEG-40 hydrogenated castor oil, PEG-16 soya sterol, polysorbate 80, polysorbate 20, polyglyceryl-3 methylglucose distearate, PEG-40 castor oil, sodium cetearyl sulphate, lecithin, laureth-4 phosphate, propylene glycol stearate SE, PEG-25 hydrogenated castor oil, PEG-54 hydrogenated castor oil, glyceryl stearate SE, PEG-6 caprylic/capric glycerides, glyceryl oleate and propylene glycol, glyceryl lanolate, polysorbate 60, glyceryl myristate, glyceryl isostearate and polyglyceryl-3 oleate, glyceryl laurate, PEG-40 sorbitan peroleate, laureth-4, glycerol monostearate, isostearyl glyceryl ether, cetearyl alcohol and sodium cetearyl sulphate, PEG-22 dodecylglycol copolymer, polyglyceryl-2 PEG-4 stearate, pentaerythrityl isostearate, polyglyceryl-3 diisostearate, sorbitan oleate and hydrogenated castor oil and cera alba and stearic acid, sodium dihydroxycetyl phosphate and isopropyl hydroxycetyl ether, methylglucose sesquistearate, methylglucose dioleate, sorbitan oleate and PEG-2 hydrogenated castor oil and ozokerite and hydrogenated castor oil, PEG-2 hydrogenated castor oil, PEG-45/dodecylglycol copolymer, methoxy PEG-22/dodecylglycol copolymer, hydrogenated cocoglycerides, polyglyceryl-4 isostearate, PEG-40 sorbitan peroleate, PEG-40 sorbitan perisostearate, PEG-8 beeswax, laurylmethicone copolyol, polyglyceryl-2 laurate, stearamidopropyl PG dimonium chloride phosphate, PEG-7 hydrogenated castor oil, triethyl citrate, glyceryl stearate citrate, cetyl phosphate polyglycerol methylglucose distearate, poloxamer 101, potassium cetyl phosphate, glyceryl isostearate, and polyglyceryl-3 diisostearates. The coemulsifiers for use in the emulsified compositions described herein include butyloctanol, butyldecanol, hexyloctanol, hexyldecanol, octyldodecanol, behenyl alcohol, cetearyl alcohol, and lanolin alcohols.

The oil phase of the emulsions can include esters of saturated and/or unsaturated, branched and/or unbranched alkanecarboxylic acids with a chain length from 3 to 30 carbon atoms; saturated and/or unsaturated, branched or unbranched alcohols with a chain length from 3 to 30 carbon atoms, from the group of the esters of aromatic carboxylic acids; and saturated and/or unsaturated, branched and/or unbranched alcohols with a chain length from 3 to 30 carbon atoms. Exemplary ester oils include isopropyl myristate, isopropyl palmitate, isopropyl stearate, isopropyl oleate, n-butyl stearate, n-hexyl laureate, n-decyl oleate, isooctyl stearate, isononyl stearate, isononyl isononanoate, 2-ethylhexyl palmitate, 2-ethylhexyl laureate, 2-hexyldecyl stearate, 2-octyldocecyl palmitate, oleyl oleate, oleyl erucate, erucyl oleate, erucyl erucate, as well as synthetic, semisynthetic, and natural mixtures of such esters, for example, jojoba oil. Additional oil phase components include branched and unbranched hydrocarbons and hydrocarbon waxes, silicone oils, dialkylethers, the group of saturated or unsaturated, branched or unbranched alcohols, as well as the fatty acid triglycerides, namely the triglycerine ester of saturated and/or unsaturated, branched and/or unbranched alkanoic acids. The fatty acid triglycerides can include, for example, synthetic, semisynthetic, and natural oils such as olive oil, sunflower oil, soy bean oil, peanut oil, rape seed oil, almond oil, palm oil, coconut oil, and palm kernel oil.

The aqueous phase of the emulsified compositions can include alcohols (e.g., ethanol or isopropanol), diols (e.g., 1,2-propanediol or 2-methyl-1,3-propanediol), or polyols having a low number of carbon atoms, and also ethers thereof, including ethanol, isopropanol, propylene glycol, glycerin, ethyleneglycol, ethyleneglycol monoethyl- or -monobutyl ether, propylene glycolmonomethyl, -monoethyl-, or -monobutyl ether, diethyleneglycol monomethyl- or -monoethyl ether.

The personal care products described herein can be provided in all the formulation forms normally available for the method of administration selected. As such, the one or more cosmetically or dermatologically acceptable materials can be of various natures depending on the type of composition considered. In some examples, the personal care products are prepared as a formulation for topical administration. The personal care products for topical administration described herein can be aqueous solutions, aqueous/alcoholic solutions, oily solutions, dispersions, emulsions, aqueous or anhydrous gels, microcapsules, microparticles, or ionic or non-ionic vesicular dispersions. For example, the personal care products can be formulated as an ointment, a liquid, a paste, a cream, a lotion, a foam, a gel, an emulsion, a powder, a shampoo, a conditioner, a hair rinse, a hair tonic, a hair spray, or a hair care treatment.

The personal care products described herein can include cleansing, protecting, treating or care creams for the face, for the hands, for the feet, for the major anatomical folds or for the body (e.g., day creams, night creams, make-up-removing creams, cream foundations, or sun creams), make-up products, such as liquid foundations, make-up-removing milks, protective or care body milks, aftersun milks, lotions, gels or foams for caring for the skin, such as cleansing or disinfecting lotions, sun lotions, artificial tanning lotions, bath compositions, deodorant compositions comprising a bactericidal agent, aftershave gels or lotions, depilatory creams, or compositions for combating insect stings and bites. Formulations for the personal care products described herein can optionally include solid formulations such as cleansing soaps and bars. These personal care products can also be formulated for scalp administration in the form of solutions, creams, gels, emulsions, foams, or aerosols. The personal care products can further be formulated as a component of a polymer matrix, a skin covering, a wound covering, a bandage, a wipe pad, or a spray.

In some examples, the polyether polyamide block copolymers and compositions can be incorporated into personal care products that protect the skin of a subject from damage resulting from UV exposure (e.g., from sunlight). The copolymers and compositions increase the SPF protection for the personal care products. In some examples, the skin of the subject is protected from sunlight with an average SPF of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50.

Gels formed from the polyether polyamide block copolymers as described herein can be used to prepare an antiperspirant or deodorant. The antiperspirant can optionally contain one or more of aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate. In some examples, the gels and the formulated antiperspirant are transparent.

The polyether polyamide block copolymer-containing gels described herein can be essentially transparent. When transparent, the gels can be combined with colorants, and optionally other ingredients, to form lipstick or other cosmetic products, without the gel interfering with or tainting the appearance of the colorant. The gels can also be used in other personal care products, e.g., cosmetics, such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, oral care bases (e.g., for toothpaste) and suppositories.

In addition, the gels of the present invention can be used in household products such as air fresheners, decorative table-top food warmers (i.e., they may be burned slowly to heat, e.g., an overhead chafing dish), automobile wax/polish, candles, furniture polish, metal cleaners/polishes, household cleaners, paint strippers and insecticide carriers.

Formulations to prepare such materials are well known in the art. For example, U.S. Pat. Nos. 3,615,289 and 3,645,705 describe candle formulations. U.S. Pat. Nos. 3,148,125 and 5,538,718 describe formulations of lipstick and other cosmetic sticks. U.S. Pat. Nos. 4,275,054, 4,937,069, 5,069,897, 5,102,656 and 5,500,209 each describe deodorant and/or antiperspirant formulations.

The polyether polyamide block copolymers described herein can be incorporated into commercial products such as those listed above, as well as into cable filling compounds, urethane/alkyl paint additives, and soaps/surfactants. These products can be prepared by blending the polyether polyamide block copolymer with the other components of the product. In these commercial products, the block copolymer can be present at a concentration of from 1% to 50% of the composition, based on the total weight of the composition. One of skill in the art can optimize the amount of block copolymer in a composition to form products with the desired consistency. In general, as more polyether polyamide block copolymer is used in a formulation, the product displays a more pronounced gel character, and forms a more rigid, or hard, gel.

The examples below are intended to further illustrate certain aspects of the methods and compositions described herein, and are not intended to limit the scope of the claims.

EXAMPLES

Example 1: Branched PAOPA Copolymer

A branched PAOPA copolymer as described herein was prepared by charging 42.15 wt. % PRIPOL 1006, a hydrogenated polymerized fatty acid (Uniqema Corporation; New Castle, Del.); 9.96 wt. % JEFFAMINE T-403, a poly(alkyleneoxy)triol-amine (54.4% base eq) (Huntsman Corporation; The Woodlands, Tex.); 1.53 wt % ethylene diamine (22.2% base eq); 46.36 wt. % JEFFAMINE M-2070, a terminating monoamine (16.7% base eq) (Huntsman Corporation; The Woodlands, Tex.); to a reactor equipped with an agitator, thermocouple probe, nitrogen inlet, and condenser. The contents of the reactor were heated to 210-215° C. and held at that temperature for 4 hours, cooled, and poured into a container. The product was a flexible, clear, near water-white solid. The softening points of the solids were measured using the ring and ball method. The amine number and acid number were measured by AQCM 069 and AQCM 001, respectively. Weight-average molecular weights of the polymers were measured by HPLC against polystyrene standards. The product had an acid number of 9.14 mg/KOH/g, an amine number of 3.6 mg/KOH/g, a softening point of 68° C., and a weight average molecular weight of 12,087 Daltons.

Example 2: Branched PAOPEA Copolymer

A branched PAOPEA copolymer as described herein was prepared by charging 47.97 wt. % PRIPOL 1006, a hydrogenated polymerized fatty acid (Uniqema Corporation; New Castle, Del.); 1.85 wt % glycerin (35.9% base eq); 2.21 wt. % ethylene diamine (43.9% base eq); 47.97 wt. % JEFFAMINE M-2070, a terminating monoamine (14.3% base eq) (Huntsman Corporation; The Woodlands, Tex.) to a reactor equipped with an agitator, thermocouple probe, nitrogen inlet, and condenser. The contents of the reactor were heated to 210-215° C. and held at that temperature for 4 hours, cooled, and poured into a container. The product was a flexible, clear, near water-white solid. The softening points of the solids were measured using the ring and ball method. The amine number and acid number were measured by AQCM 069 and AQCM 001, respectively. Weight-average molecular weights of the polymers were measured by HPLC against polystyrene standards. The product had an acid number of 19.5 mg/KOH/g, an amine number of 0.67 mg/KOH/g, a softening point of 77° C., and a weight average molecular weight of 10,038 Daltons.

Example 3: Gelation Test of Examples 1 and 2

The branched copolymers prepared according to Examples 1 and 2 were combined with various polar liquids at a 10 wt % copolymer concentration. The polar liquids included a 50/50 propylene glycol/water blend; tripropylene glycol; 1,3-butylene glycol; methylpropanediol; propylene glycol; PEG 400 polyethylene glycol; FINSOLV TN (Innospec Active Chemicals; Newark, Del.); and ethyl hexyl acetate. The mixtures were heated with stirring to about 80-100° C. to yield a clear solution. The resulting mixtures were then cooled to room temperature and the firmness and clarity of the mixture was determined. The results are shown in Table C below. In Table C, "gel" means the test mixture at room temperature was immobile, even if vigorously shaken, and transparent. "Jelly" means the mixture was mobile upon inverting and shaking its container, "Paste" or "pasty" refers to mixtures that were soft, opaque, and did not have a desired gel consistency; however, the mixtures designated as "paste" or "pasty" were not fluid, thus indicating marginal polymer compatibility with the test liquid. Both of Examples 1 and 2 were able to affect the rheology of relatively higher polarity liquids.

TABLE C

|  | Example 1 | Example 2 |
|---|---|---|
| Propylene Glycol and Water (50:50) | Soluble | Soluble |
| Tripropylene Glycol | Soft gel | Soft gel |
| 1,3 Butylene Glycol | Cloudy liquid | Cloudy liquid |
| Methylpropanediol | Clear gel | Clear gel |
| Propylene Glycol | Hazy gel | Clear gel |
| PEG 400 Polyethylene glycol | Hazy gel | Hazy gel |
| FINSOLV TN | Clear gel | Clear gel |
| Ethyl Hexyl Acetate | Jelly | Soft gel |

Example 4: Sunscreen Lotion Formulation Including Example 1

The branched copolymer of Example 1 was prepared in a sunscreen lotion. Water (53.46 wt. %) and 2.00 wt. % AVICEL PC 611, a microcrystalline cellulose commercially available from FMC BioPolymer (Philadelphia, Pa.) were mixed and slowly heated to 85° C. over 20 minutes to form Phase A.

Example 1 (4.00 wt. %); 5.01% of butylene glycol; 10 wt. % of LEXPEEL 7, a neopentyl glycol diheptanoate commercially available from Inolex Chemical Company (Philadelphia, Pa.); 3.00 wt % of EUSOLEX 9020, a butyl methoxydibenzoylmethane commercially available from EMD Chemical (Gibbstown, N.J.); and 2.00 wt. % SOLASTAY, an ethylhexyl methoxycrylene commercially available from The Hallstar Company (Chicago, Ill.) were mixed together to form Phase B.

Z-COTE HP-1 (9.99%), a zinc oxide/triethoxycaprylsilane mixture commercially available from BASF Corporation (Florham Park, N.J.), and 8.04% of DC 200 350 CST, a dimethicone commercially available from Dow Corning (Midland, Mich.), were mixed together for five minutes on high speed, until homogenous, using a Hamilton Beach Homogenizer (Richmond, Va.) to form Phase C.

Phase C was slowly added to phase B while maintaining a temperature between 75° C. 85° C. The combined phases were then added to Phase A until uniform. A silica HDI trimethylol hexylactone crosspolymer (2.00 wt. %), commercially available as BPD-500W from KOBO Products (South Plainfield, N.J.) was then added and the resulting mixture was homogenized for 3 minutes at high speed. The mixture was then cooled to room temperature and 0.50 wt % of phenoxyethanol (PHENONIP; Clariant, Muttenz, Switzerland) was mixed to form the sunscreen lotion.

Example 5: Sunscreen Lotion Formulation Including Example 2

The branched copolymer of Example 2 was prepared in a sunscreen lotion. Water (53.26 wt. %) and 1.99 wt, % AVICEL PC 61 1were mixed and slowly heated to 85° C. over 20 minutes to form Phase A. Example 2 (4.00 wt, %), 4.99% of butylene glycol, 9.96 wt. % of LEXFEEL 7, 3.01 wt % of EUSOLEX 9020, and 2.24 wt. % SOLASTAY were mixed together to form Phase B. Z-COTE HP-1 (9.95%) and 8.09% of DC 200 350 CST were mixed together for five minutes on high speed, until homogenous, using a Hamilton Beach Homogenizer to form Phase C. Phase C was slowly added to phase B while maintaining a temperature between 75-85° C. The combined phases were then added to Phase A until uniform. BPD-500W (1.99 wt. %) was then added and the resulting mixture was homogenized for 3 minutes at high speed. The mixture was then cooled to room temperature and 0.52 wt % of PHENONIP was mixed to form the sunscreen lotion.

The compositions, methods, and apparatuses of the appended claims are not limited in scope by the specific compositions, methods, and articles described herein, which are intended as illustrations of a few aspects of the claims and any compositions, methods, and articles that are functionally equivalent are intended to fall within the scope of the claims. Various modifications of the compositions, methods, and articles in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents can be explicitly mentioned herein; however, other combinations of steps, elements, components, and constituents are included, even though not explicitly stated. Furthermore, where a range of values is provided, all the whole number values within that range are disclosed herein. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

What is claimed is:

1. A polyether polyamide block copolymer having the following formula:

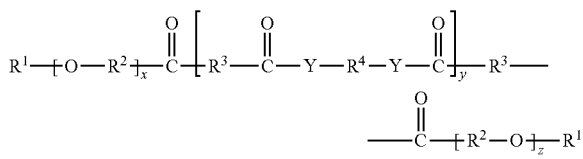

wherein $R^1$ is a $C_1$-$C_8$ hydrocarbon radical, $R^2$ is a $C_2$-$C_4$ hydrocarbon diradical, $R^3$ is a $C_2$-$C_{52}$ hydrocarbon diradical, $R^4$ is selected from $C_2$-$C_{12}$ hydrocarbon diradicals optionally substituted with alkylene oxide groups, wherein at least a portion of the $R^4$ groups is substituted with Y—C(=O)—$R^3$—C(=O)—Z—$(R^2$—O$)_w$—$R^1$, wherein Y is O or NH, Z is O or NH, w is an integer from 2 to 100; x is an integer from 2 to 100; y is an integer from 1 to 10, and z is an integer from 2 to 100, and wherein at least a portion of the Y groups is NH, wherein the softening point of the polyether polyamide block copolymer is from 60° C. to 150° C. and a viscosity of less than 5,000 centipoise at 160° C., wherein the polyether polyamide block copolymer is prepared from reactants comprising a $C_2$-$C_{12}$ aliphatic diamine and a trifunctional component, wherein the trifunctional component is selected from triols, triamines, and mixtures thereof, and the diamine is present in amounts of 50% or less based on the total amount of difunctional and trifunctional amines and alcohols present on an equivalents basis.

2. The block copolymer of claim 1, wherein in at least a portion of the $R^4$ groups substituted with Y—C(=O)—$R^3$—C(=O)—Z—$(R^2$—O$)_w$—$R^1$, Y is O.

3. The block copolymer of claim 2, wherein at least a portion of the $R^4$ groups is a $C_3$ diradical substituted with O—C(=O)—$R^3$—C(=O)—Z—$(R^2$—O$)_w$—$R^1$.

4. The block copolymer of claim 1, wherein in at least a portion of the $R^4$ groups substituted with Y—C(=O)—$R^3$—C(=O)—Z—$(R^2$—O$)_w$—$R^1$, Y is NH.

5. The block copolymer of claim 4, wherein at least a portion of the $R^4$ groups is a $C_6$ diradical substituted with alkylene oxide groups and NH—C(=O)—$R^3$—C(=O)—Z—$(R^2$—O$)_w$—$R^1$.

6. The block copolymer of claim 1, wherein the weight average molecular weight is from 5000 to 30,000.

7. The block copolymer of claim 1, wherein the softening point is 60° C. to 140° C.

8. A polyether polyamide block copolymer having the following formula:

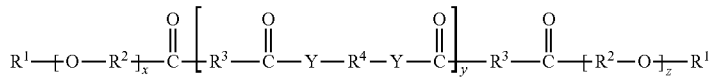

wherein $R^1$ is a $C_1$-$C_8$ hydrocarbon radical, $R^2$ is a $C_2$-$C_4$ hydrocarbon diradical, $R^3$ is a $C_2$-$C_{52}$ hydrocarbon diradical, $R^4$ is selected from $C_2$-$C_{12}$ hydrocarbon diradicals optionally substituted with alkylene oxide groups, wherein at least a portion of the $R^4$ groups is substituted with Y—C(=O)—$R^3$—C(=O)—Z—$(R^2$—O$)_w$—$R^1$, wherein Y is O or NH, Z is O or NH, and w is an integer from 2 to 100; x is an integer from 2 to 100; y is an integer from 1 to 10, and z is an integer from 2 to 100, produced by reacting a dibasic acid; a $C_2$-$C_{12}$ aliphatic diamine; a tri-functional component selected from the group consisting of triols, triamines, and mixtures thereof: and a monofunctional poly(alkyleneoxy) monoamine, wherein the diamine is present in an amount of 50% or less based on the total amount of difunctional and trifunctional amines and alcohols present on an equivalents basis, wherein the polyether polyamide block copolymer has a softening point from 60° C. to 150° C. and a viscosity of less than 5,000 centipoise at 160° C.

9. The block copolymer of claim 8, wherein the trifunctional component includes glycerin.

10. The block copolymer of claim 8, wherein the trifunctional component includes a poly(alkyleneoxy) triamine.

11. The block copolymer of claim 10, wherein the trifunctional component is a C6 triamine substituted with oxypropylene groups.

12. The block copolymer of claim 8, wherein the weight average molecular weight is from 5000 to 30,000.

13. The block copolymer of claim 1, wherein at least a portion of the $R^4$ groups are substituted with O—C(=O)—$R^3$—C(C=O)—Z—$(R^2$—O$)_w$—$R^1$.

14. The block copolymer of claim 1, wherein at least a portion of the $R^4$ groups are substituted with Y—C(=O)—$R^3$—C(C=O)—Z—$(R^2$—O$)_w$—$R^1$.

15. The block copolymer of claim 1, wherein at least 50 mol % of the $R^3$ groups are $C_{34}$ hydrocarbon diradicals.

* * * * *